United States Patent
Muramatsu et al.

(10) Patent No.: US 10,761,105 B2
(45) Date of Patent: Sep. 1, 2020

(54) AUTOMATIC ANALYZING APPARATUS

(71) Applicant: Hitachi High-Technologies Corporation, Tokyo (JP)

(72) Inventors: Yoshiki Muramatsu, Tokyo (JP); Takamichi Mori, Tokyo (JP); Kazuhiro Nakamura, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 545 days.

(21) Appl. No.: 15/325,519

(22) PCT Filed: Jun. 15, 2015

(86) PCT No.: PCT/JP2015/067112
§ 371 (c)(1),
(2) Date: Jan. 11, 2017

(87) PCT Pub. No.: WO2016/009765
PCT Pub. Date: Jan. 21, 2016

(65) Prior Publication Data
US 2017/0176484 A1    Jun. 22, 2017

(30) Foreign Application Priority Data
Jul. 18, 2014   (JP) .................................. 2014-147294

(51) Int. Cl.
*G01N 35/10* (2006.01)
*G01N 21/11* (2006.01)
(Continued)

(52) U.S. Cl.
CPC .......... *G01N 35/1079* (2013.01); *G01N 21/11* (2013.01); *G01N 21/25* (2013.01);
(Continued)

(58) Field of Classification Search
CPC .......... G01N 35/1079; G01N 33/4875; G01N 21/11; G01N 21/25; G01N 2035/0494;
(Continued)

(56) References Cited

U.S. PATENT DOCUMENTS 4,854,355 A    8/1989   Chazot et al.
5,216,926 A    6/1993   Lipscomb
(Continued)

FOREIGN PATENT DOCUMENTS

| EP | 0 452 892 A2 | 10/1991 |
| JP | 2001-228161 A | 8/2001 |
| JP | 2002-286728 A | 10/2002 |

OTHER PUBLICATIONS

International Search Report of PCT/JP2015/067112 dated Sep. 29, 2015.
(Continued)

*Primary Examiner* — Daniel S Larkin
*Assistant Examiner* — Anthony W Megna Fuentes
(74) *Attorney, Agent, or Firm* — Mattingly & Malur, PC

(57) ABSTRACT

An automatic analyzing apparatus is provided which includes a member 401 fixed at a predetermined level which presses down the sample container sealed with the sealing plug that is floated from the rack due to friction between the probe and the sealing plug when pulling out the probe from the sample container sealed with the sealing plug, and a mechanism 402 that pushes down, toward the rack, the sample container sealed with the floated sealing plug in which the sample container sealed with the floated sealing plug is transported by the transport line, and disposed on a path of the transport line until re-inspection is performed after pulling out the probe from the sample container sealed with the sealing plug.

14 Claims, 7 Drawing Sheets

(51) Int. Cl.
*G01N 21/25* (2006.01)
*G01N 33/487* (2006.01)
*G01N 35/04* (2006.01)
*G01N 33/49* (2006.01)
*G01N 33/493* (2006.01)

(52) U.S. Cl.
CPC ......... *G01N 33/4875* (2013.01); *G01N 33/49* (2013.01); *G01N 33/493* (2013.01); *G01N 2035/0405* (2013.01); *G01N 2035/0412* (2013.01); *G01N 2035/0494* (2013.01)

(58) Field of Classification Search
CPC ... G01N 2035/0412; G01N 2035/0405; G01N 33/493; G01N 33/49
See application file for complete search history.

(56) References Cited

U.S. PATENT DOCUMENTS

| | | | |
|---|---|---|---|
| 5,483,843 A | 1/1996 | Miller et al. | |
| 5,665,309 A * | 9/1997 | Champseix | G01N 35/04 141/130 |
| 7,282,182 B2 * | 10/2007 | Dale | B01L 9/06 422/562 |
| 7,322,525 B2 * | 1/2008 | Itoh | G01N 35/00732 235/462.43 |
| 2003/0017084 A1 | 1/2003 | Dale et al. | |
| 2006/0216208 A1 | 9/2006 | Li et al. | |
| 2008/0274551 A1 * | 11/2008 | Chinchilla | G01N 35/025 436/2 |
| 2012/0294765 A1 * | 11/2012 | Watabe | G01N 35/0092 422/65 |
| 2013/0136569 A1 | 5/2013 | Rosmarin et al. | |
| 2013/0209333 A1 | 8/2013 | Nuotio et al. | |

OTHER PUBLICATIONS

Extended European Search Report received in corresponding European Application No. 15821622.6 dated Feb. 16, 2018.

* cited by examiner

AUTOMATIC ANALYZING APPARATUS

TECHNICAL FIELD

The present invention relates to an automatic analyzing apparatus having a sample dispensing device, and more particularly to an automatic analyzing apparatus that pierces a sealing plug of a test tube and dispenses a sample without performing an opening process.

BACKGROUND ART

In the automatic analyzing apparatus, for example, in an automatic biochemical analyzer, in order to perform a component analysis of a biological sample (hereinafter referred to as "sample") such as serum or urine, a sample and a reagent are reacted with each other, and a change in a color tone and turbidity caused by the reaction is optically measured by a photometric unit such as a spectrophotometer.

In order to react the sample with the reagent, there is a need to dispense the sample and the reagent into a reaction chamber from containers in which the respective sample and reagent are contained. In order to achieve the dispensing, the automatic analyzing apparatus is equipped with a dispensing device that automatically suctions and discharges the sample or the reagent into the reaction chamber from the containers in which the respective sample and reagent are contained.

A blood collection tube (hereinafter referred to as a "sample container") used for collecting a sample such as blood is sealed with a sealing plug such as a rubber stopper. In the automatic biochemical analyzer that automatically measures the sample without performing the opening process of the sample container, there is a need to perform the operation of piercing the rubber stopper with a sharp probe to suction the sample, and pulling out the probe from the rubber stopper to discharge the sample. However, when pulling out the probe from the rubber stopper, the sample container lifts up due to friction between the probe and the rubber stopper.

As means for preventing lifting up, in a technique disclosed in Patent Literature 1, a mechanism for holding the sample container during the piercing operation and the pulling operation of the probe is provided separately from an elevating mechanism of the probe. The piercing operation and the pulling operation of the probe are performed while an upper surface of the sample container is held by the mechanism for holding the sample container.

CITATION LIST

Patent Literature

Patent Literature 1: Japanese Unexamined Patent Application Publication No. 2001-228161

SUMMARY OF INVENTION

Technical Problem

According to the method disclosed in Patent Literature 1 described above, there is a need to install a vertically driven pressing mechanism at a suction position of the sample where the probe is vertically driven in addition to a vertical mechanism of the probe. This may cause the structure and the adjustment to be complicated and the costs to be increased.

Against this problem, a fixed plate having a hole shape into which the probe can be inserted is installed between the sample container and the probe at the suction position of the probe, thereby being capable of avoiding the lifting of the sample container. More specifically, when the probe suctions and moves down the sample container mounted on a sample rack, the probe passes through the hole shape of the fixed plate and is inserted into the sample container. When the probe lifts up after having suctioned the sample, the probe and the sample container lift up integrally due to friction between the probe and the rubber stopper of the sample container. In this case, when a size of the hole shape of the fixed plate is set to be smaller than a diameter of the sample container, a lid portion of the sample container is pressed down on the fixed plate, and only the probe can be pulled out.

In this example, a spring is incorporated into the sample rack so that a sample barcode label affixed to the sample container is not rotated in the sample rack to hold down the sample container. When the probe lifts up after suctioning, the sample container is integrated with the probe and lifts up, and is held down by the fixed plate as described above. However, because the spring is incorporated into the sample rack, after the probe has been inserted into and pulled out from the sample container, the sample container is held in a floating state from the sample rack, and moved from the suction position.

However, in the sample for which an automatic re-inspection (automatic re-inspection) is requested, the sample is kept in the apparatus after the analysis has been completed. If a measurement result falls within a range, the sample is unloaded, but if the measurement result falls outside the range, the analysis is again implemented. In this situation, the sample container mounted on the sample rack, which is kept in the apparatus, is held in the floating state, and when the sample rack is again moved to the suction position for the automatic re-inspection, it is conceivable that the floating sample container comes in contact with the fixed plate, and causes the apparatus to stop. This is because a level of an upper surface of the floating sample container becomes higher than a level of a lower surface of the fixed plate due to a vibration during transport while the sample container is again moved to the suction position from the suction position.

Also, when the probe is moved down from the state in which the sample container is floated from the sample rack, the probe is inserted into the sample container in a bent state, to thereby degrade the reliability of the device due to an influence of a damage of the probe, a dispensing accuracy, scattering, or the like.

Further, in the case of the automatic analyzing apparatus having multiple analyzer, or in the case where the sample is suctioned at multiple suction positions even if only one analyzer is provided, if the sample container is floated from the rack between transports of the analyzer or between the suction positions, the floated sample container comes in contact with the fixed plate to stop the device or damage the probe at a next analyzer or a next suction position as in the above case. Therefore, it is desirable to push down the floated sample container toward the rack regardless of whether the automatic re-inspection is requested or not.

The present invention has been made in view of the above problem, and therefore an object of the present invention is to push down a sample container floated due to friction between a probe and a sealing plug such as a rubber stopper when pulling out the probe toward a rack.

Solution to Problem

In order to solve the above problem, for example, a configuration defined by the claims is applied.

The present invention includes multiple solutions to the above problem, and one example of the solutions will be described below.

In an automatic analyzing apparatus including a transport line for transporting a sample container with a rack on which the sample container is mounted, and a probe that suctions a sample from the sample container and discharges the sample into a reaction vessel in which a sealing plug is pierced with the probe from the sample container sealed with the sealing plug, the sample is suctioned by the probe, and the sample is pulled out and discharged by the probe, the automatic analyzing apparatus includes: a member fixed at a predetermined level which presses down the sample container sealed with the sealing plug that is floated from the rack due to friction between the probe and the sealing plug when pulling out the probe from the sample container sealed with the sealing plug; and a mechanism that pushes down the sample container sealed with the floated sealing plug toward the rack in which the sample container sealed with the floated sealing plug is transported by the transport line, and disposed on a path of the transport line until re-inspection is performed after pulling out the probe from the sample container sealed with the sealing plug.

Also, another example will be described below.

In an automatic analyzing apparatus including a transport line for transporting a sample container with a rack on which the sample container is mounted, and a probe that suctions a sample from the sample container and discharges the sample into a reaction vessel in which a sealing plug is pierced with the probe from the sample container sealed with the sealing plug, the sample is suctioned by the probe, and the sample is pulled out and discharged by the probe, the automatic analyzing apparatus includes: a member fixed at a predetermined level which presses down the sample container sealed with the sealing plug that is floated from the rack due to friction between the probe and the sealing plug when pulling out the probe from the sample container sealed with the sealing plug; and a mechanism that pushes down the sample container sealed with the floated sealing plug toward the rack in which the sample container sealed with the floated sealing plug is transported by the transport line after pulling out the probe from the sample container sealed with the sealing plug.

In the present specification, the "fixed at a predetermined level" means a distinction from a sample container holding mechanism of a type in which a member for pressing down a sample container is driven up and down, and means that the member is not driven up and down. In other words, the "member fixed at a predetermined height" means a member that is not connected to a driving mechanism that drives the member up and down, and does not change the predetermined level.

Advantageous Effects of Invention

According to the present invention, contact of the floated sample container with an interior of the apparatus can be avoided by the raised sample container by pushing down the sample container which has floated up due to the friction between the probe and the sealing plug when pulling out the probe. Also, an automatic analyzing apparatus with high reliability without damaging the probe can be provided.

The problems, configurations, and advantageous effects other than those described above will be clarified from the description of embodiments below.

DESCRIPTION OF EMBODIMENTS

Hereinafter, embodiments will be described with reference to the drawings.

First Embodiment

Figure 1:
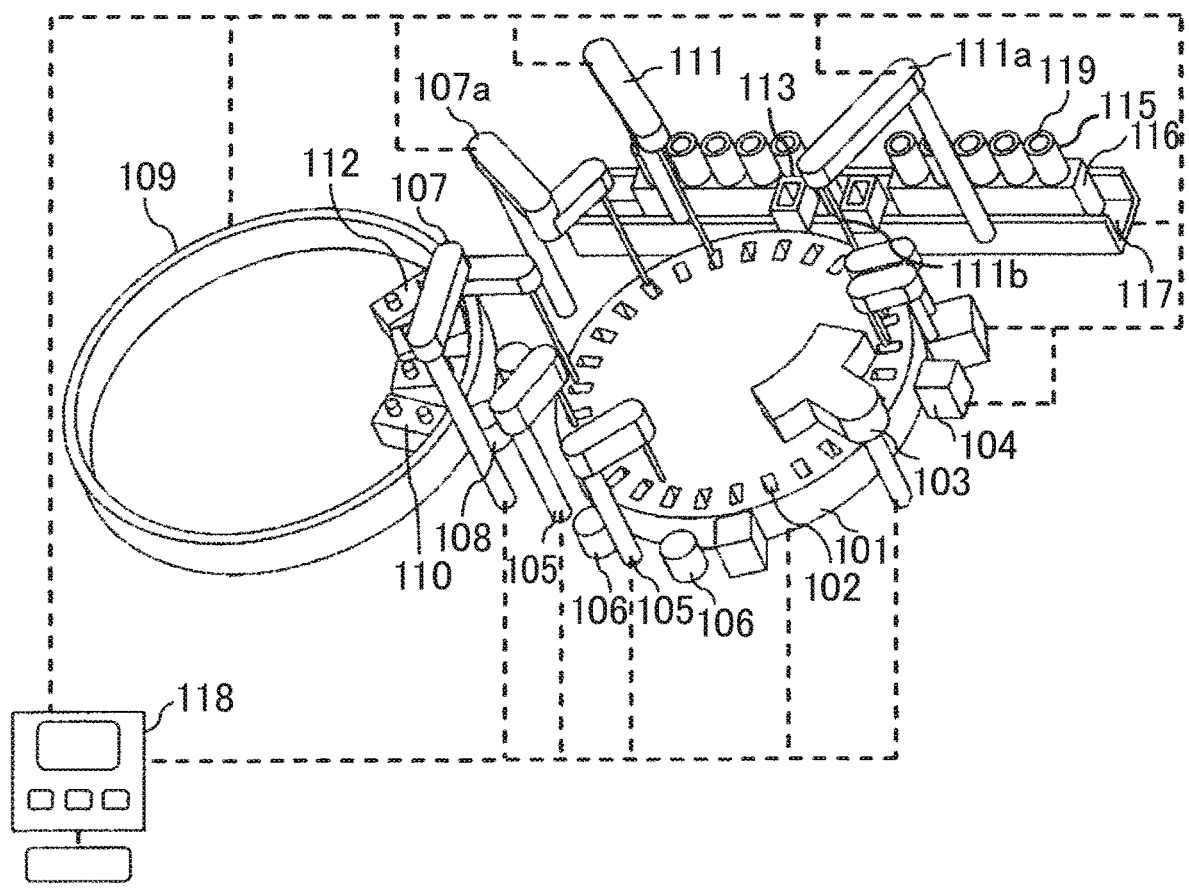
FIG. 1 is a schematic configuration diagram of an automatic analyzing apparatus according to the present invention.

Referring to FIG. 1, an automatic analyzing apparatus is schematically configured by a reaction disk 101, a cleaning mechanism 103, a spectrophotometer 104, a stirring mechanism 105, a cleaning bath (stirring mechanism) 106 (for the stirring mechanism 105), a first reagent dispensing mechanism 107, a second reagent dispensing mechanism 107a, a cleaning tank 108 (the first reagent dispensing mechanism 107 and the second reagent dispensing mechanism 107a), a reagent storage 109, sample dispensing mechanisms 111, 111a, a probe 111b of the sample dispensing mechanism 111a, a cleaning tank 113 (for the sample dispensing mechanisms 111 and 111a), a sample transport mechanism 117, a control unit 118, and so on.

As illustrated in FIG. 1, reaction vessels 102 are circumferentially arranged on the reaction disk 101. The reaction vessels 102 are containers for accommodating a mixed solution obtained by mixing and reaching a sample and a reagent, and the multiple reaction vessels 102 are arranged on the reaction disk 101.

The sample transport mechanism 117 for moving the sample rack 116 on which the sample container 115 sealed with the rubber stopper 119 is disposed in the vicinity of the reaction disk 101. The cleaning mechanism 103, the spectrophotometer 104, the stirring mechanism 105, and so on are disposed around the reaction disk 101.

In addition to multiple reagent bottles 110 and multiple detergent bottles 112, the reagent storage 109 has a structure in which bottles for accommodating a diluent and a pretreatment reagent can be circumferentially arranged.

The cleaning mechanism 103 is a mechanism that suctions the mixed liquid whose measurement has been completed by the spectrophotometer 104 and cleans an inside of each reaction vessel 102.

The spectrophotometer 104 is a measuring unit for measuring an absorbance of a measurement light that has passed through the mixed solution in each reaction vessel 102. The reaction disc 101 is rotated to pass an optical axis of the spectrophotometer 104 through the reaction disk 101 at regular intervals, and the spectrophotometer 104 measures the absorbance of the mixed solution in each reaction vessel 102 each time. Then, in the control unit 118 to be described later, a concentration of a target component in the sample is calculated on the basis of the measured absorbance and a calibration curve prepared in advance. Note that the spectrophotometer 104 may calculate not the passed light but a scattered light. In other words, the spectrophotometer 104 may measure any one of the transmitted light and the scattered light as long as the spectrophotometer 104 receives light irradiated from a light source (not shown) via the mixed solution.

The sample dispensing mechanisms 111 and 111a capable of rotating and moving up and down are disposed between the reaction disk 101 and the sample transport mechanism 117. The sample dispensing mechanisms 111 and 111a are moved while drawing circular arcs around each rotation axis, and dispense a sample from the sample container 115 to the reaction vessels 102. One or a plurality of sample dispensing mechanisms 111 and 111a are installed respectively, and in the present embodiment, two sample dispensing mechanisms 111 and 111a are provided.

The first reagent dispensing mechanism 107 and the second reagent dispensing mechanism 107a capable of rotating and moving up and down are disposed between the reaction disc 101 and the reagent storage 109. The reagent dispensing mechanisms 107 and 107a move with rotation about a single axis or multiple axes around each rotation axis, and dispense a reagent, a detergent, a diluent, a pretreatment reagent from the reagent bottles 110, the detergent bottles 112, a diluent bottle, a pretreatment reagent bottle, and the like into the reaction vessels 102. One or multiple first reagent dispensing mechanisms 107 and the second reagent dispensing mechanisms 107a are installed. The present embodiment shows an example in which one first reagent dispensing mechanism 107 and one second reagent dispensing mechanism 107a are installed.

The reagent dispensing mechanisms 107 and 107a operate to suction the detergent from the reagent storage 109 and discharge the detergent to the reaction container 102 to be rewashed at the time of re-cleaning the reaction container 102.

The control unit 118 controls the operation of the respective mechanisms in the automatic analyzing apparatus, such as the rotation of the reaction disk 101, the operation of driving, suctioning and discharging the sample dispensing mechanisms 111, 111 a and the reagent dispensing mechanisms 107, 107 a, the transport of the sample container 115, the reagent bottles 110, the detergent bottles 112, and so on. The control unit 118 outputs the concentration of the target component of the sample on the basis of the output of the spectrophotometer 104.

Figure 2:
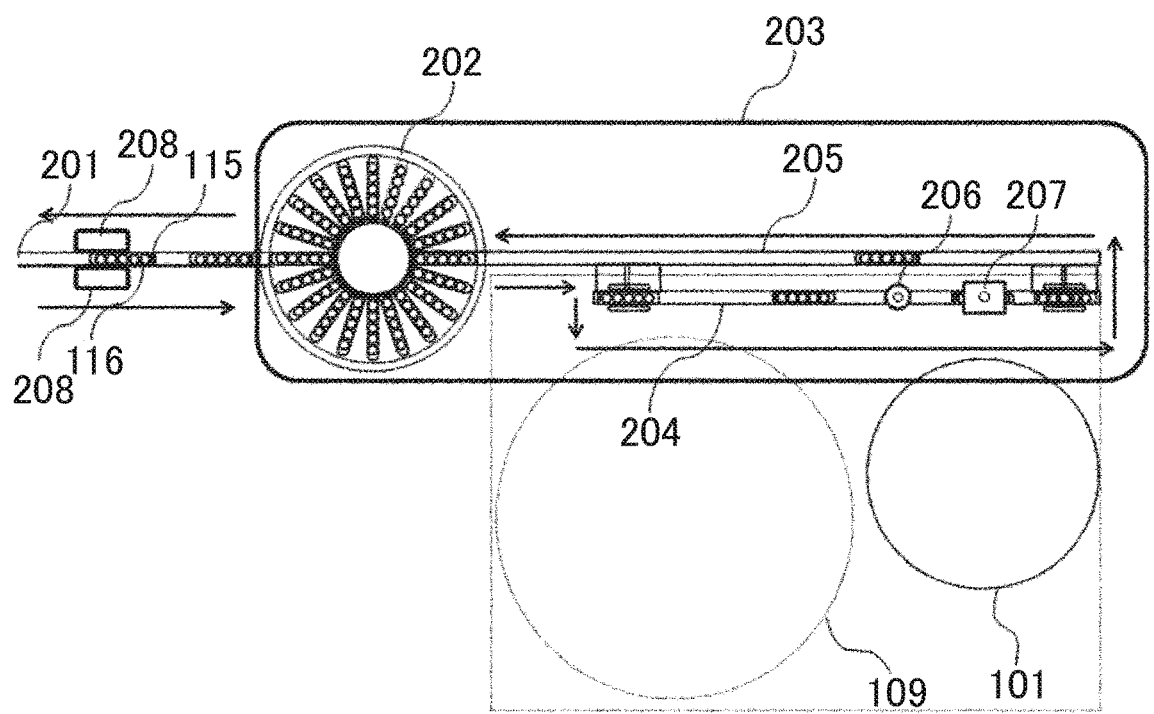
FIG. 2 is a schematic diagram of a transport mechanism for transporting a sample rack on which multiple sample containers each holding a sample can be mounted.

FIG. 2 is a schematic diagram of a transport mechanism for transporting the sample rack on which the multiple sample containers each holding the sample can be mounted.

Referring to FIG. 2, the transport mechanism includes a loading port 201 for loading the sample rack 116 on which mounting the multiple sample containers 115 for holding the samples can be mounted, a level measurement position 208 of the sample container, a rack loader 202 that can hold the multiple sample racks 116 on which mounting the multiple sample containers 115 for holding the samples can be mounted, and a transport line 203. The transport line includes a loading line 204 (sub-transport line) and a loading/unloading line 205 (main transport line) as well as a suction position 206 and a suction position 207 on the loading line 204. The loaded sample rack 116 first enters the rack loader 202 and is held in the rack loader 202. The sample rack 116 is then transported to the loading line 204 via the loading/unloading line 205 and stopped at the dispensing position 207. After the sample has been dispensed into the sample rack 116 by the probe 111b of the dispensing mechanism 111a, the sample rack 116 passes through the loading/unloading line 205, and unloaded from the loading port 201 through the rack loader 202. The sample for which an automatic re-examination is requested is subjected to a first dispensing at the suctioning position 207, and waits in the rack loader 202 until a result of the inspection is determined through the loading/unloading line 205. If the inspection result falls outside a range, the same sample waiting in the rack loader 202 returns again to the suction position 207 to perform the analysis. The sample which has been analyzed is unloaded from the apparatus through the loading port 201.

Figure 3:
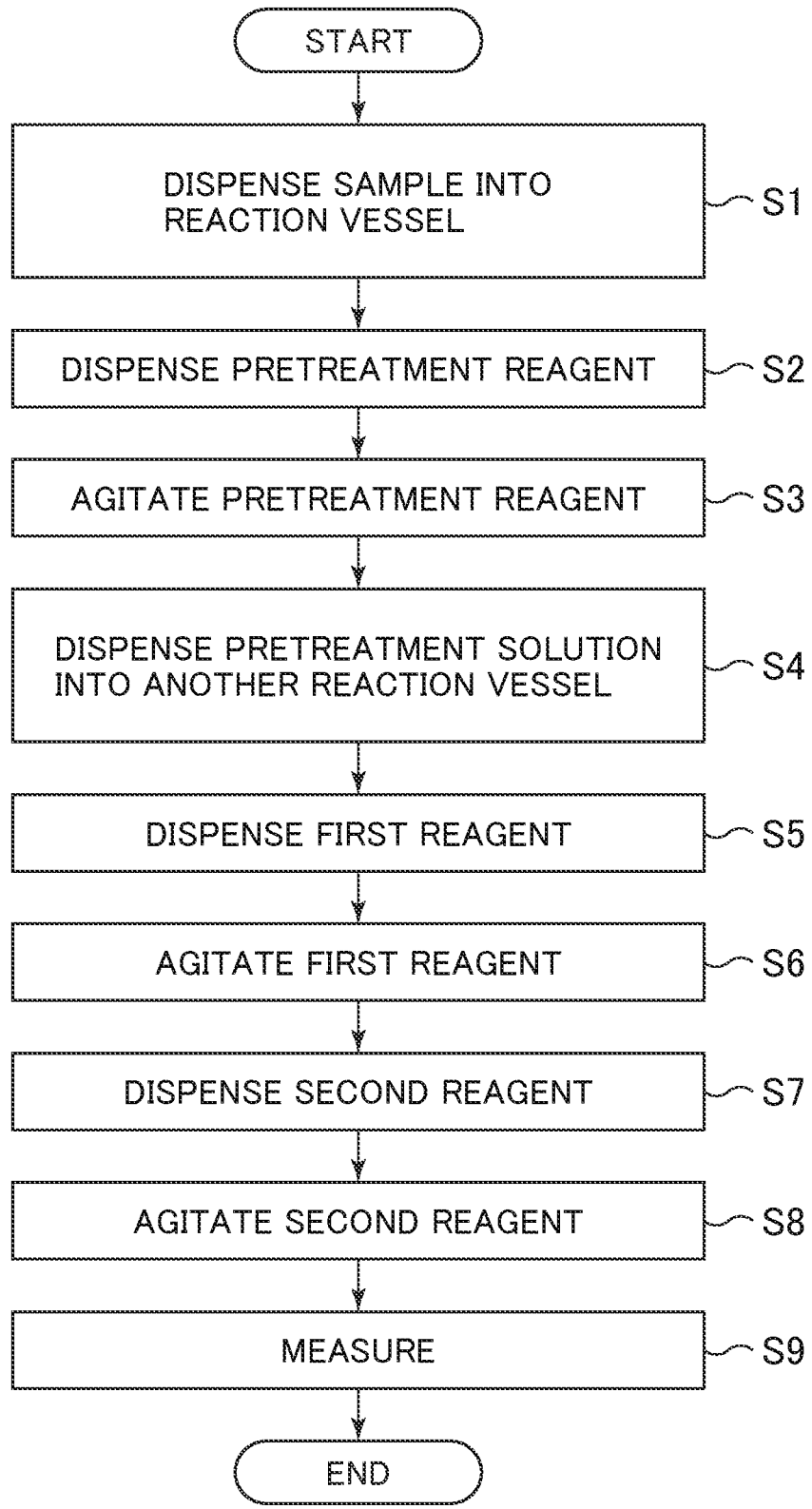
FIG. 3 is an illustrative view of a main portion (mechanism for pushing down the sample container) according to an embodiment of the present invention.

A flow of the analysis operation in the automatic analyzing apparatus according to the present invention will be described with reference to FIG. 3.

First, the sample dispensing mechanism 111a, the sample transport mechanism 117 and the reaction disk 101 are controlled so that the sample contained in the sample container 115 set in the sample rack 116 is dispensed into each of the reaction vessels 102, and a fixed amount of sample is dispensed (Step S1).

Next, in order to perform a pretreatment step, the second reagent dispensing mechanism 107a, the reagent storage 109, and the reaction disc 101 are controlled to perform dispensing so as to dispense a pretreatment reagent to each of the reaction vessels 102 (Step S2).

Next, the stirring mechanism 105 and the reaction disk 101 are controlled to perform stirring so as to stir a mixed solution of the pretreatment reagent and the sample in each reaction vessel 102 into which the pretreatment reagent is dispensed (Step S3).

Next, the sample dispensing mechanism 111 and the reaction disk 101 are controlled to perform dispensing so that a pretreatment solution after stirring the pretreatment reagent and the sample is dispensed into another reaction vessel 102a (not shown) (Step S4).

Next, the first reagent dispensing mechanism 107, the reagent storage 109, and the reaction disk 101 are controlled to perform dispensing so as to dispense the first reagent into the reaction vessel 102a (Step S5).

Next, the stirring mechanism 105 and the reaction disk 101 are controlled to perform stirring so as to stir the mixed solution in the reaction vessel 102a into which the first reagent is dispensed (Step S6).

Next, the first reagent dispensing mechanism 107 or the second reagent dispensing mechanism 107a, the reagent storage 109, and the reaction disk 101 are controlled to perform dispensing so as to dispense the second reagent (Step S7).

Next, the stirring mechanism 105 and the reaction disk 101 are controlled to perform stirring so as to stir the mixed solution in the reaction vessel 102a into which the second reagent is dispensed (Step S8).

Next, the spectrophotometer 104 and the reaction disk 101 are controlled to perform measurement so as to measure an absorbance of the mixed liquid in the reaction vessel 102a (Step S9). The reaction disc 101 repeats rotation and stop periodically, and the measurement is performed at timing when each reaction vessel 102 passes a front of the spectrophotometer 104. In the actual measurement, a process of reaction of the mixed solution from the addition of the first reagent is measured.

Figure 4:
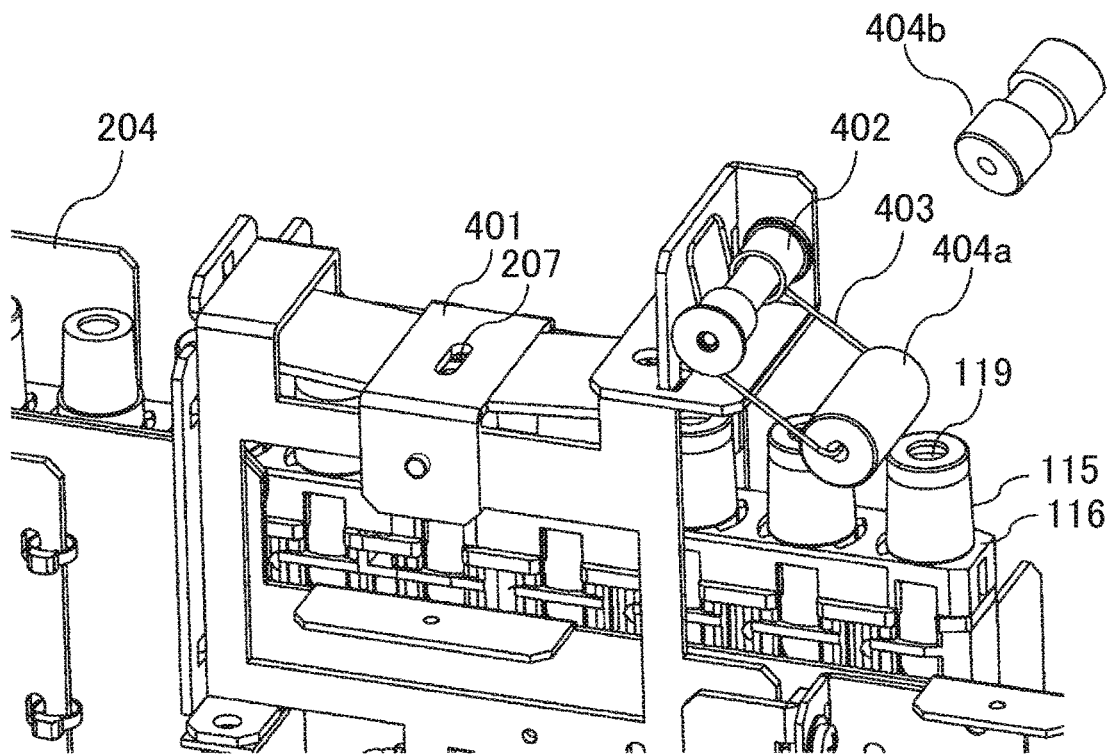
FIG. 4 is a flowchart of analysis operation in the automatic analyzing apparatus according to the present invention.

FIG. 4 is an illustrative view of a main portion (mechanism for pushing down the sample container) according to an embodiment of the present invention.

The push-down mechanism 402 includes a contact portion that comes into contact with the rubber stopper 119 in order to push down the sample container, and a case in which the contact portion is a roller 404a will be described with reference to FIG. 4.

In FIG. 4, a plate 401 (a member for pressing down the sample container) is installed at a level where the sample container 115 mounted on the sample rack 116 in advance does not come into contact with the plate 401, at the suction position 207 located on the loading line 204. In order to press down the floating of the sample container 115, which is integrated due to the friction between the probe 111b and the rubber stopper 119, from the sample rack 116 at the time of moving up the probe 111b after the probe 111b has been inserted into the sample container 115, the plate 401 has an opening of the size as large as the rubber stopper 119 of the sample container 115 cannot pass through the opening to press down the floating. Also, the push-down mechanism 402 is provided to press down the sample container 115 that has been floated up to the plate 401 for pressing down the floating due to the friction between the probe 111b and the rubber stopper 119 to the rack. The push-down mechanism 402 includes the spring 403 and the roller 404a.

It should be noted that the spring 403 may be replaced with an elastic member such as rubber if the spring 403 is formed of an elastic member. The plate 401 for pressing down the floating is not limited to a plate but a shape of the member for pressing down the floating is not limited to the plate shape. Hereinafter, for the sake of convenience, the elastic member will be described as a spring, and the pressing member will be described as a plate.

The sample rack 115 loaded from the loading port 201 first enters the rack loader 202 and is held in the rack loader 202. The sample rack 115 is then transported to the loading/unloading line 205 (main transport line), thereafter transported to the loading line 204 (sub-transport line), and stops at the suction position 207.

At the suction position 207, the probe 111b is moved down and passes through a hole formed in the plate 401 which presses down floating and penetrates the rubber stopper 119. After the penetration, the sample dispensing mechanism 111 is moved down into the sample container 115, and the sample is suctioned into the probe 111b in a state where a tip of the probe 111b is immersed in the sample. Thereafter, when the probe 111b is moved up, the sample container 115 which has been floated integrally with the probe 111b due to the friction between the probe 111b and the rubber stopper 119 is pressed down by the plate 401 for pressing down the floating, and the probe 111b is pulled out from the rubber stopper 119 and moved onto the reaction vessel 102 to discharge the sample. On the other hand, the floated sample container 115 is pushed down to the sample rack 116 by the push-down mechanism 402 after the sample has been dispensed at the suction position 207, transported to the rack loader 202, and unloaded.

The sample for which the automatic re-inspection is requested self-repair inspection waits in the rack loader 202 until the measurement result is output without being unloaded to the outside of the apparatus after the first dispensation. If the inspection result falls within a range of normal values, the sample is unloaded, and if the inspection result falls out of the range, the sample is again transported to the suction position 207, dispensed, and analyzed.

All of the sample containers 115 floating from the sample rack 116 are pushed down by the push-down mechanism 402, thereby being capable of preventing the sample container 115 from coming into contact with the plate 401 that presses down the floating and stopping the apparatus when the sample rack 116 is loaded onto the suction position 207 at the time of automatic re-inspection.

Figure 5:
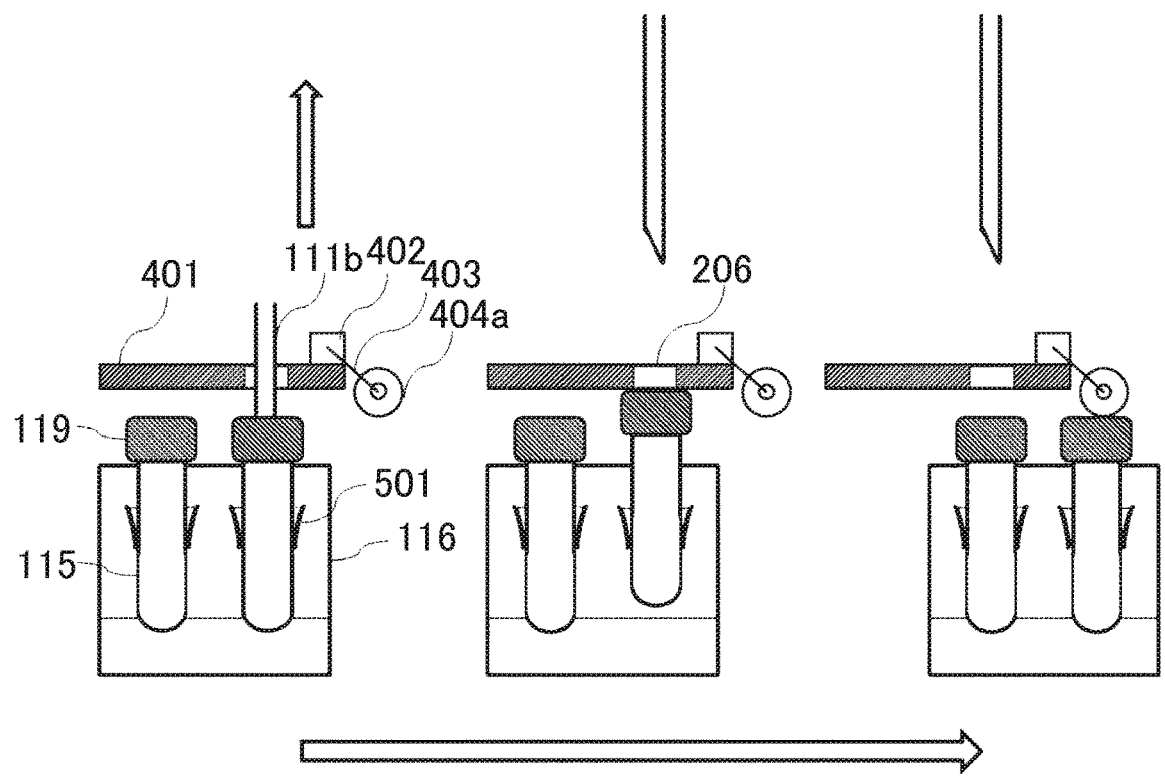
FIG. 5 is a diagram illustrating the operation of pushing down a floated sample container by a spring and a roller.

FIG. 5 is a diagram illustrating the operation of pushing down the floated sample container by the spring 403 and the roller 404a. The roller 404a is a roller that rotates in the transport direction of the sample rack 116.

In FIG. 5, when the probe 111b moves down to the sample container 115 mounted on the sample rack 116 for suctioning, the probe 111b passes through the hole shape of the plate 401 which presses down the floating, and the probe 111b pierces the sealing plug and is inserted into the sample container. When the probe 111b is moved up after having suctioned the sample, the probe 111b and the sample container 115 are moved up integrally due to the friction. In this situation, when a size of the hole shape of the plate 401 for pressing down the floating is set to be smaller than a diameter of the sample container 115, a lid portion of the sample container 115 is pressed down by the plate 401 which presses down the floating so that only the probe 111b can be pulled out. In this example, a spring 501 is incorporated in the sample rack 116 so that the bar code affixed to the sample container 115 does not rotate in the sample rack 116, to hold the sample container 115. For that reason, when the probe 111b is moved up after having suctioned the sample, the sample container 115 is moved up integrally with the probe 111b, and pressed down by the plate 401 for pressing down the floating, and the sample container 115 is held in a floated state from the sample rack 116. When the sample rack 116 in which the sample container 115 is held in the floated state is transported, the floated sample container 115 comes into contact with the roller 404a of the push-down mechanism 402 configured by the spring 403 and the roller 404a. In this situation, when the sample rack 116 in which the sample container 115 is held in the floated state while keeping the contact state is further transported, a force for lifting upward is exerted on the roller 404a by the aid of the sample container 115, and the roller 404a moves upward. For that reason, the roller 404a pushes down the sample container 115 to the sample rack 116 due to a reaction generated when the spring 403 connected to the roller 404a is compressed.

With the above configuration, when the sample rack is again transported to the suction position 207 at the time of automatic re-inspection, the sample container 115 is prevented from coming into contact with the plate 401 for pressing down the floating to stop the apparatus, and the measurement of the apparatus can be prevented from being stopped. It is desirable that a distance between the plate 401 for pressing down the floating located above the sample container 115 and the sample container 115 is set to 1 to 5 mm. If the distance is too longer, a reaction force of the spring 403 must be increased. When the reaction force of the spring 403 is increased, it can be supposed that a stop position of the sample rack 116 is displaced, and the displacement leads to an error of the stop position when suctioning a next sample, and the probe 111b may be damaged. It is ideal that the sample container 115 is surely pushed down to the sample rack 116. However, if the sample container 115 can be prevented from coming into contact with the plate 401 for pressing down the floating at the time of automatic re-inspection even if slight floating occurs, the measurement of the apparatus can be prevented from being stopped. Further, when the sample container 115 is slightly floated, the probe 111b comes into contact with the rubber stopper 119 and pushes out the rubber stopper 119 toward the sample rack 116 during the dispensing operation at the time of re-inspection. However, if the floating of about 1 mm occurs, because the sample container 115 is pressed down by the spring 501 within the sample rack 116, the sample container 115 is not largely inclined with respect to the probe 111b. Hence, the slight floating is available because the probe 111b is not bent. In addition, because the spring is used for the mechanism 302 for pushing down the sample container 115, a length of the sample containers 115 does not need to be uniformed, and various types of sample containers are available.

Also, a shape of the roller for pushing down the sample container 115 is not limited to the roller 404a illustrated in FIG. 4. For example, a description will be given with reference to the roller 404b illustrated in FIG. 4.

In the illustrative view, the roller 404b is a roller recessed in the vicinity of the center of the roller that pushes down the floated sample container.

In the roller 404b, the roller is recessed at a position where the probe 111b is inserted into the rubber stopper 119 of the sample container 115. In this way, an insertion/pull-out position of the probe in an upper portion of the sample container 115 is prevented from coming into contact with the probe, thereby being capable of avoiding the contamination of the roller and other sample containers. In this case, if the roller can be brought into contact with an edge of the rubber stopper of the sample container 115, which is a position out of the insertion/pull-out position, the advantageous effects of the present invention can be obtained.

With the employment of the above roller, the transport line is transported without stopping at the mechanism 402 for pushing down the sample rack 116, as a result of which the roller that is a contact portion can push down the floated sample container. In other words, there is no need to stop the sample rack 116 only for the purpose of pushing down the floated sample container. It should be noted that as illustrated in FIG. 4, when the push-down mechanism 402 is placed close to the suction position, the floating of the sample container different from the dispensing target can be pushed down with the movement of the sample rack for changing the dispensing target within the sample rack. In this case, the push-down mechanism 402 may be located immediately above the sample container in a state where the sample rack is stopped, but the sample rack is not stopped only for the purpose of pushing down the sample container. Even in this case, the transport line transports the sample rack 116 without stopping the sample rack 116 with the push-down mechanism 402, whereby the roller that is the contact portion pushes down the floated sample container.

In addition, in the above description, an example of the spring and the roller is described. In other words, in the description of the present embodiment, the push-down mechanism 402 includes the contact portion that comes into contact with the sealing plug and the elastic member that is connected with the contact portion, and the transport line transports the sample rack to compress the elastic member, and the contact portion can push down the floated sample container due to the compressed reaction force.

Also, in the above description, as the roller 404b, the contact portion is shaped such that the contact portion does not come into contact with the probe insertion/pull-out position of the sealing plug, but comes into contact with a position of the sealing plug out of the insertion/pull-out position. Similarly, in the following examples, such a shape is desirable.

Now, the plate 401 for pressing down the floating will be described. As illustrated in FIG. 4, the plate 401 for pressing down the floating is fixed to the suction position. In other words, the plate is fixed to a predetermined level, and is not connected to a drive mechanism that drives in a vertical direction. Therefore, the sample container is resultantly floated from the sample rack, and the push-down mechanism 402 for pushing down the sample container is available.

As described above, in the present embodiment, the automatic analyzing apparatus includes the member fixed to the predetermined level, which presses down the sample container sealed with the sealing plug floating from the sample rack due to the friction between the sample probe and the sealing plug when the sample probe is pulled out from the sample container sealed with the sealing plug, and the mechanism that pushes down, to the rack, the sample container sealed with the floated sealing plug in which the sample container sealed with the floated sealing plug is transported by the transport line and disposed on a path of the transport line until re-inspection is performed, after the sample probe has been pulled out from the sample container sealed with the sealing plug.

In addition, the mechanism for pushing down the sample container 115 is not limited to the configuration illustrated in FIG. 5. The mechanism will be described, for example, with reference to FIGS. 6, 7, and 8.

Figure 6:
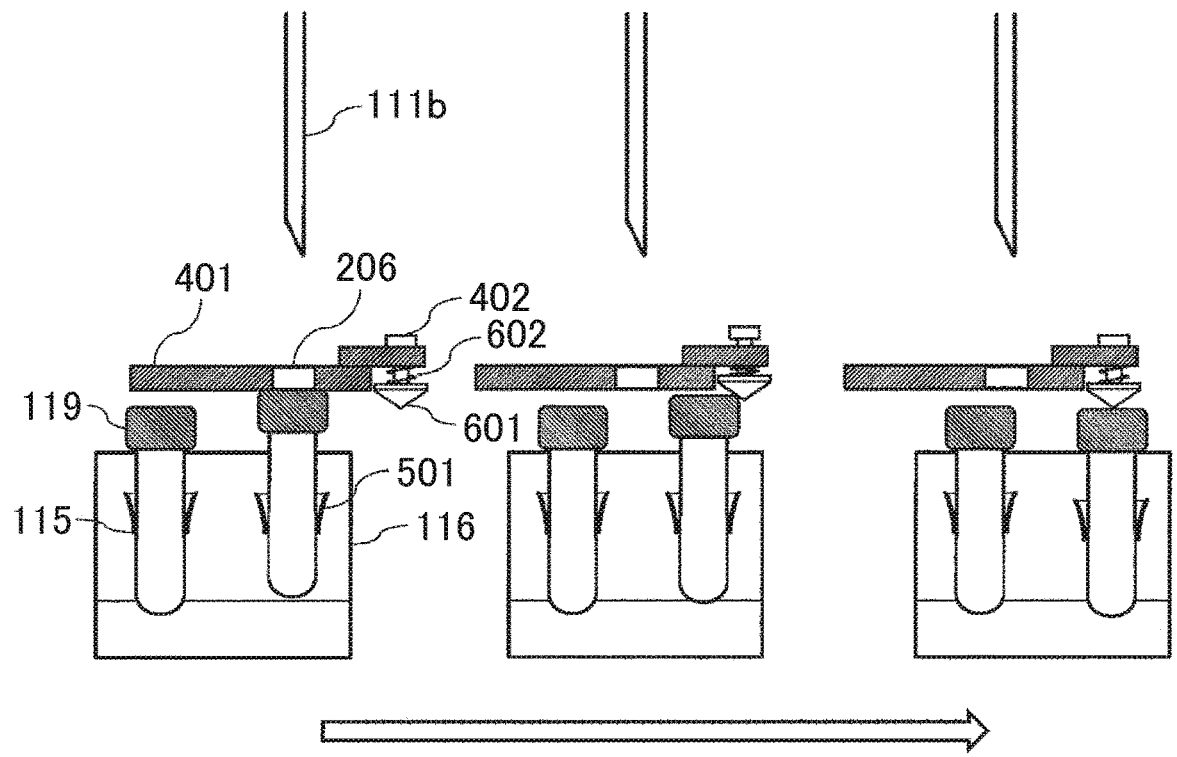
FIG. 6 is a diagram illustrating the operation of pushing down the floated sample container by a spring and a block.

FIG. 6 is a diagram illustrating the operation of pushing down the floated sample container by a spring and a block.

Referring to FIG. 6, the push-down mechanism 402 includes a block 601 and a spring 602. When the sample rack 116 held in a state where the sample container 115 is floated up to the plate 401 for pressing down the floating by the probe 111b is transported, the floated sample container 115 comes into contact with the block 601. In this situation, when the sample rack 116 held in a state where the sample container 115 is floated is further transported while keeping the contact state, a force for lifting the block 601 upward by the sample container 115 is exerted. For that reason, a structure in which the sample container 115 is pushed down to the sample rack 116 due to a reaction force generated by compressing the spring 602 connected to the block 601 can be provided. It is desirable that the block 601 is of a rotating structure. For example, the block 601 having a structure such as the roller described above can be provided. This is because a force applied to the block 601 at the time of contacting the sample rack is dispersed, and the dispersion of the force enables the sample rack to be smoothly transported.

Also, in this case, it is desirable that the block 601 is inclined. In other words, it is desirable that the block has an inclination whose distance to the transport line becomes shorter toward the transport direction of the sample rack. With the above configuration, when the sample rack is again transported to the suction position 207 at the time of automatic re-inspection, the sample container 115 can be prevented from coming into contact with the plate 401 for pressing down the floating and stopping the apparatus, and the measurement of the apparatus can be prevented from being stopped.

In addition, it is desirable that a distance between the plate 401 for pressing down the floating which is located above the sample container 115 and the sample container 115 is set to 1 to 5 mm. If the distance is too long, a reaction force of the spring 602 must be increased. If the reaction force of the spring 602 is increased, it can be supposed that the stop position of the sample rack 116 is displaced, and the displacement leads to an error of the stop position when suctioning a next sample, and the probe 111b may be damaged.

It is ideal that the sample container 115 is surely pushed down to the sample rack 116. However, if the sample container 115 can be prevented from coming into contact with the plate 401 for pressing down the floating at the time of automatic re-inspection even if slight floating occurs, the measurement of the apparatus can be prevented from being stopped.

Further, when the sample container 115 is slightly floated, the probe 111b comes into contact with the rubber stopper 119 and pushes out the rubber stopper 119 toward the sample rack 116 during the dispensing operation at the time of re-inspection. However, if the floating of about 1 mm occurs, because the sample container 115 is pressed down by the spring 501 within the sample rack 116, the sample container 115 is not largely inclined with respect to the probe 111b. Hence, the slight floating is available because the probe 111b is not bent. In addition, because the spring is used for the mechanism 402 for pushing down the sample container 115, a length of the sample containers 115 does not need to be uniformed, and various types of sample containers are available.

In the example using the block, similarly to the example using the roller, the sample container can be transported without any stoppage by the mechanism 402 for pushing down the sample rack.

Figure 7:
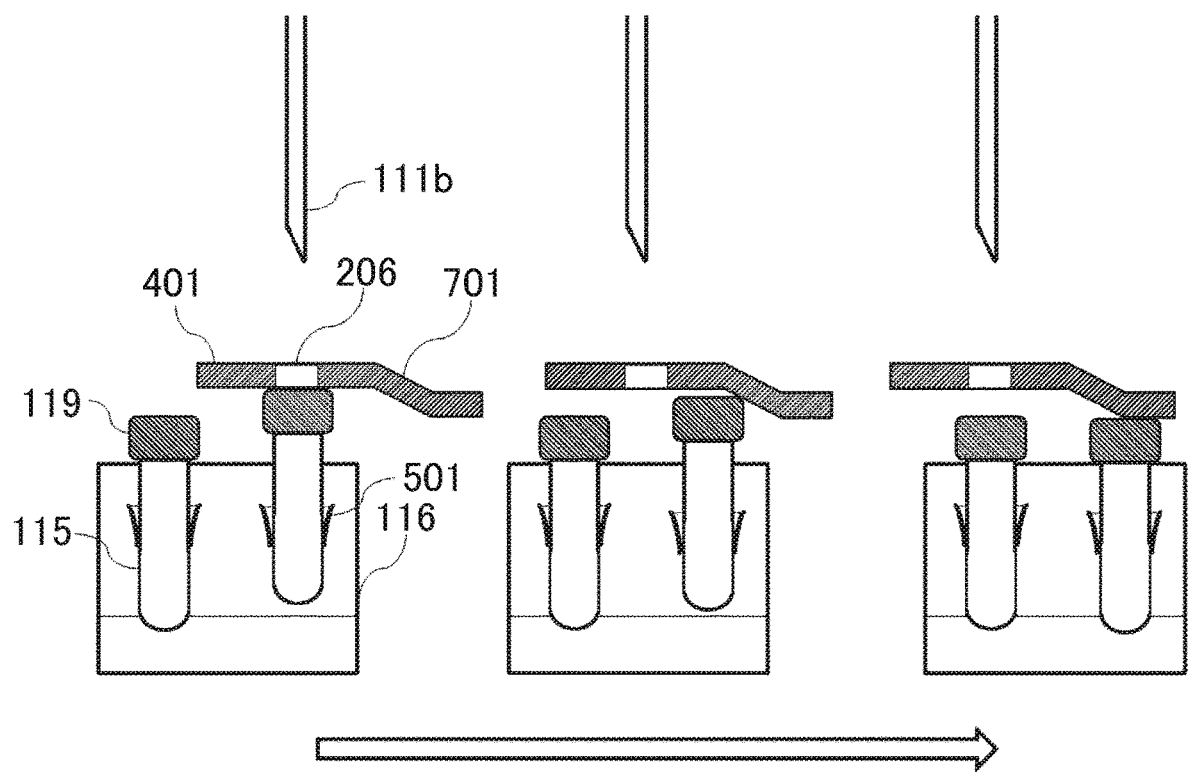
FIG. 7 is a diagram illustrating the operation of pushing down the floated sample container by a slope.

FIG. 7 is a diagram illustrating the operation of pushing down the floated sample container by a slope, which is an example using the slope as the contact portion.

Referring to FIG. 7, the push-down mechanism 402 is equipped with a slope 701. As shown in the figure, the slope has an inclination whose distance from the transport line becomes shorter toward the transport direction of the sample rack. When the sample rack 116 held in a state where the sample container 115 is floated up to the plate 401 for pressing down the floating by the probe 111b is transported, an upper surface (an edge of the upper surface) of the sealing plug of the floated sample container 115 comes into contact with the slope 701. In this situation, a mechanism in which the sample rack 116 held in a state where the sample container 115 is floated is further transported while keeping the contact state, as a result the sample container 115 is pushed down to the sample rack 116 along the inclination of the slope 701 can be provided.

With the above configuration, when the sample rack is again transported to the suction position 207 at the time of automatic re-inspection, the sample container 115 can be prevented from coming into contact with the plate 401 for pressing down the floating and stopping the apparatus, and the measurement of the apparatus can be prevented from being stopped.

In addition, it is ideal that the sample container 115 is surely pushed down to the sample rack 116. However, if the sample container 115 can be prevented from coming into contact with the plate 401 for pressing down the floating at the time of automatic re-inspection even if slight floating occurs, the measurement of the apparatus can be prevented from being stopped.

Further, when the sample container 115 is slightly floated, the probe 111b comes into contact with the rubber stopper 119 and pushes out the rubber stopper 119 toward the sample rack 116 during the dispensing operation at the time of re-inspection. However, if the floating of about 1 mm occurs, because the sample container 115 is pressed down by the spring 501 within the sample rack 116, the sample container 115 is not largely inclined with respect to the probe 111b. Hence, the slight floating is available because the probe 111b is not bent.

In FIG. 7, the slope is integrated with the plate 401 for pressing down the floating. However, the slope may be configured by another member different from the plate 401 for pressing down the floating. The integration can reduce the number of parts.

Figure 8:
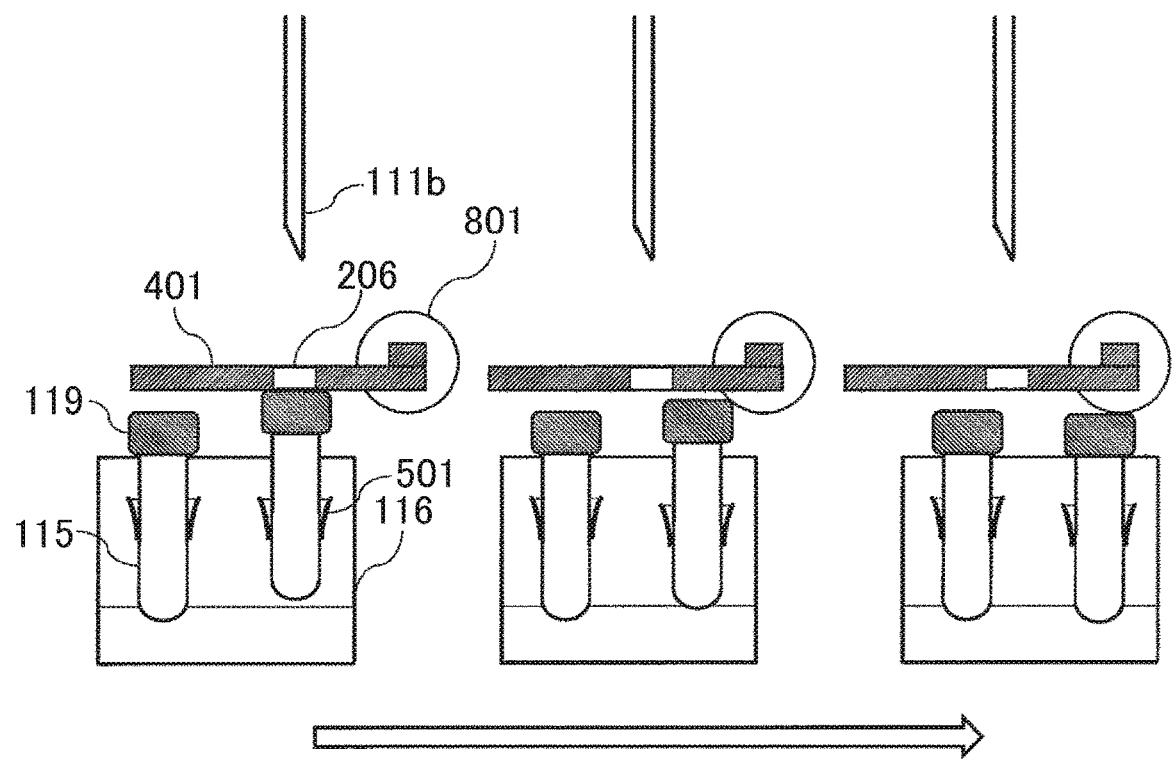
FIG. 8 is a diagram illustrating the operation of pushing down the floated sample container by a fixed roller.

FIG. 8 is a diagram illustrating the operation of pushing down the floated sample container by a fixed roller when the roller is employed as the contact portion. The roller rotates in the transport direction of the sample rack, which is not connected with the spring that is an elastic member and fixed unlike FIG. 5.

Referring to FIG. 8, the push-down mechanism 402 is equipped with a roller 801. When the sample rack 116 held in a state where the sample container 115 is floated up to the plate 401 for pressing down the floating by the probe 111b is transported, an upper surface of the sealing plug of the floated sample container 115 comes into contact with the roller 801. In this situation, a mechanism in which the sample rack 116 held in a state where the sample container 115 is floated is further transported while keeping the contact state, as a result of which the sample container 115 is pushed down to the sample rack 116 along the shape of the roller can be provided. As a result, the same advantages as those described above can be obtained.

Further, the number of mechanisms for pushing down the floated sample container 115 does not need to be one, but may be multiple. For example, the configuration will be described, for example, with reference to FIG. 9.

Figure 9:
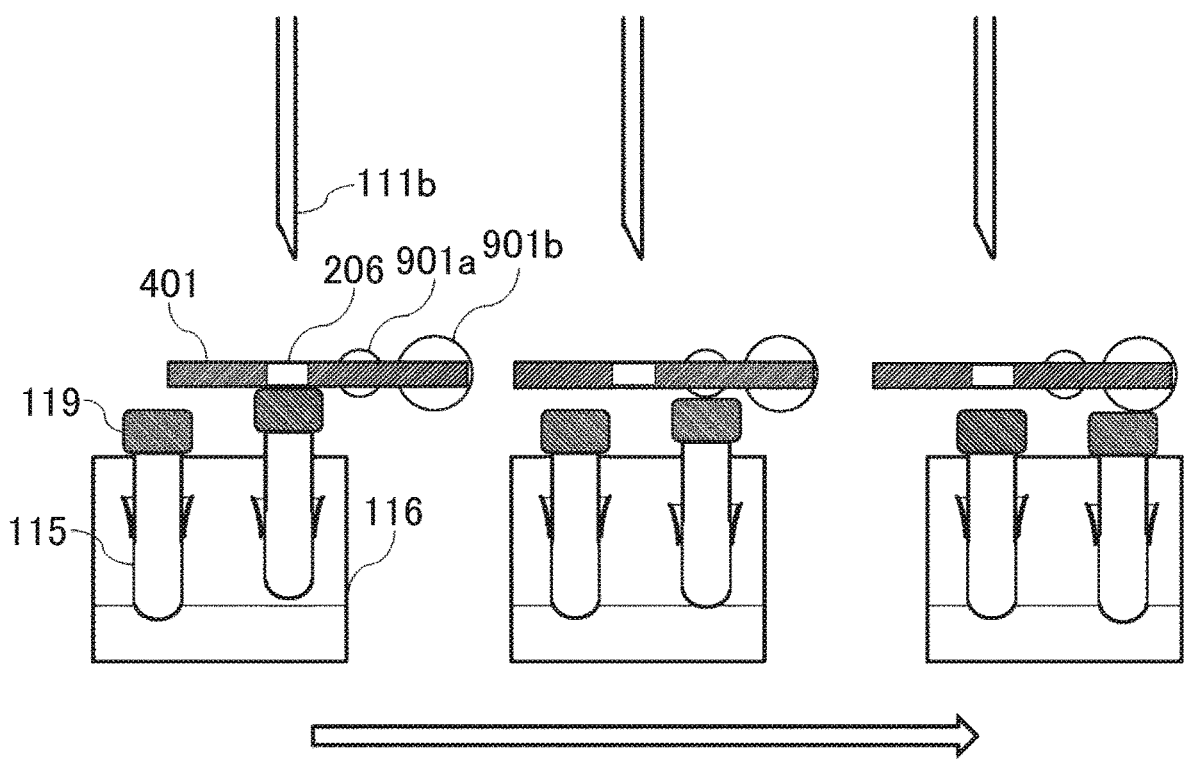
FIG. 9 is a diagram illustrating the operation of pushing down the floated sample container by two fixed rollers step by step.

FIG. 9 is a diagram illustrating the operation of pushing down the floated sample container by two fixed rollers step by step. The two rollers rotate in the transport direction of the sample rack. Meanwhile, the spring 403 may be installed in each of those rollers as illustrated in FIG. 5.

Referring to FIG. 9, the push-down mechanism 402 is equipped with rollers 901a and 901b. When the sample rack 116 held in a state where the sample container 115 is floated up to the plate 401 for pressing down the floating by the probe 111b is transported, the floated sample container 115 comes into contact with the roller 901a. In this situation, the sample rack 116 held in a state where the sample container 115 is floated is further transported while keeping the contact state, as a result of which the sample container 115 is pushed down to a lower portion of the roller 901a along the shape of the roller 901*a*. When the sample rack 116 held in a state where the sample container 115 is pushed down to the lower portion of the roller 901*a* by the roller 901*a* is transported, the floated sample container 115 comes into contact with the roller 901*b*. In this situation, the sample rack 116 is further transported in the contact state, to thereby push down the sample container 115 to the sample rack 116 along the shape of the roller 901*b*. In this example, the roller 901*a* smaller in diameter than the roller 901*b* may be used. In addition, for the sake of convenience, two rollers are used. However, the number of rollers to be used may be set to two or more, and the sample container 115 may be moved down step by step. With this configuration, the same advantages as those described above can be obtained.

Further, the sample container 115 is pushed down step by step, thereby being pushed down to the sample rack 116 with applying less load to the apparatus.

In other words, when generalizing the example of the roller, the contact portion includes the first contact portion and the second contact portion, and the second contact portion is located downstream of the first contact portion in the transport direction of the sample rack, and a distance between the second contact portion and the transport line is shorter than a distance between the first contact portion and the transport line. With the above configuration, even in the case other than the roller, the sample container 115 can be pushed down step by step.

It is preferable that the rollers used in FIGS. 4 to 9 is made of a resin such as Teflon (registered trademark) having high chemical resistance or ultra-high polymer preethylene having a low friction coefficient, but the same advantages can be obtained even if a metal such as SUS is used. This is because the generation of abrasion powder from a rubber stopper cover or the like can be suppressed by optimizing a transport speed of the sample rack or the like.

Further, in the embodiment described above, the mechanism for pushing down the floated sample container 115 is fixed on the transport line 203, and the sample rack 116 on which the sample container 115 is mounted passes through the push-down mechanism to push down the floated sample container 115. In the configurations described above, the floating of the sample container can be pushed down without a need of the drive source, which is effective in configuration. However, the present invention is not limited to the above configuration. For example, the configuration will be described, for example, with reference to FIG. 10.

Figure 10:
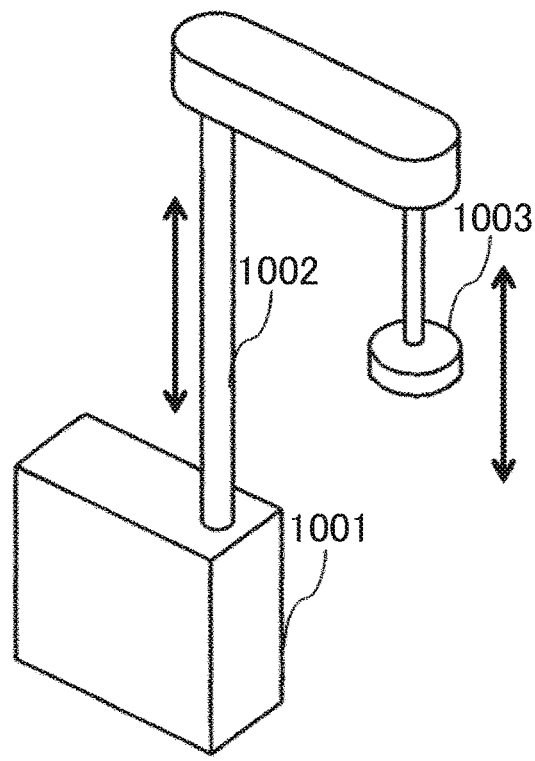
FIG. 10 is a diagram illustrating the operation of pushing the floated sample container into the sample rack with the transmission of a power to a mechanism for pushing down the floated sample container.

FIG. 10 is a diagram illustrating the operation of pushing the floated sample container into the sample rack with the transmission of power to a mechanism for pushing down the floated sample container. FIG. 10 shows an example in which a block is employed as the contact portion.

Referring to FIG. 10, the push-down mechanism 402 is equipped with a motor 1001, a movable portion 1002 movable by the motor, and a block 1003 installed on the movable portion 1002 on a transfer line 203. The sample rack 116 held in a state where the sample container 115 is floated up to the plate 401 for pressing down the floating by the probe 111*b* is transported to below the block 1003 and stops once. A structure in which the movable portion 1002 is movable by the motor, the block 1003 is moved down, and the floated sample container 115 is pushed to the sample rack 116 can be provided. The floated sample containers 115 are not necessarily pushed into the sample rack 116 one by one, but multiple floated sample container 115 may be pushed into the sample rack 116 in bulk. In other words, the push-down mechanism 402 includes a contact portion that comes into contact with the sealing plug and a drive source that drives the contact portion, and power is transmitted to the contact portion from the drive source, to thereby push down the floated sample container. As a result, the drive source such as a motor is necessitated, but the same advantages as those described above can be obtained.

In the above description, the mechanism 402 for pushing down the floated sample container 115 is installed on the loading/unloading line 205. However, the present invention is not limited to the above configuration. For example, the push-down mechanism 402 may be installed immediately before the sample rack 116 is transported to the suction position 207 if the push-down mechanism 402 is disposed on the transport line 203 again transmitted from the suction position 207 to the suction position 207. Since the sample rack 116 does not move to the level measurement position 208 side of the rack loader 202 until the re-inspection is performed, in the example of FIG. 2, the push-down mechanism 402 may be arranged in any place downstream of the suction position 207, and upstream of the loading/unloading line 205, the rack loader 202, the suction Or upstream of position 207, may be arranged.

Figure 11:
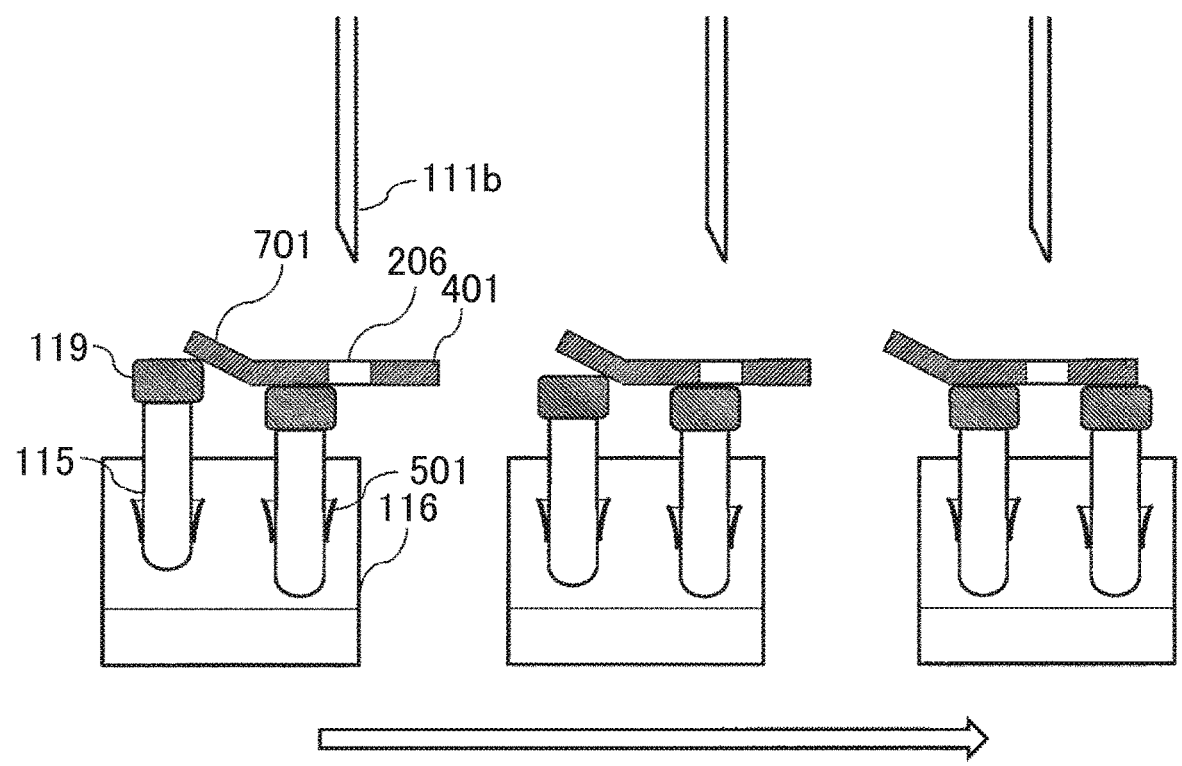
FIG. 11 is a diagram illustrating a configuration in which the mechanism for pushing down the floated sample container is disposed immediately before the suction position.

Referring to FIG. 11, an example in which the mechanism for pushing down the floated sample container is located immediately before the suction position 207, in other words, an example in which the mechanism for pushing down the floated sample container is located upstream of the suction position 207 will be described. FIG. 11 illustrates an example in which a slope is located upstream of the suction position 207 whereas FIG. 7 illustrates an example in which the slope is employed as the contact portion. In the example of FIG. 7, the slope pushes down the sample container 115 floated up to the level of the plate 401 for pressing down the floating below the level of the plate 401. On the other hand, in the example of FIG. 11, the slope pushes down the sample container 115 floated up to the level of the plate 401 for pressing down the floating to the plate 401 for pressing down the floating.

FIG. 11 is a diagram illustrating the operation of pushing down the floated sample container by a slope 701. For example, the slope 701 is provided on the loading line 204. The illustrated sample container is a sample which has already been dispensed once at the suction position 207, which shows an appearance immediately before the sample container is again transported to the suction position 207 because the inspection result falls outside the range. In other words, the sample container is again transported to a position immediately before the suction position 207 in a state where the sample container has been already floated up to the plate 401 for pressing down the floating. In this situation, as described with reference to the above problem, the level of the upper surface of the floating sample container becomes higher than the level of the lower surface of the fixed plate due to a vibration during transport while the sample container is again moved to the suction position 207 from the suction position 207, and the sample container illustrated is a sample container in this case.

As shown in the figure, the slope 701 has an inclination whose distance from the transport line becomes shorter toward the transport direction of the sample rack. An upper surface (an edge of the upper surface) of the sealing plug of the floated sample container 115 comes into contact with the slope 701. The sample rack 116 is further transported while keeping the contact state, thereby being capable of pushing down the sample container to the sample rack 116 along the inclination of the slope 701.

With the above configuration, when the sample rack is again transported to the suction position 207 at the time of automatic re-inspection, the sample container 115 can be prevented from coming into contact with the plate 401 for pressing down the floating to stop the apparatus, and the measurement of the apparatus can be prevented from being stopped.

It is ideal that the sample container is surely pushed down to the sample rack 116. However, if the sample container can be prevented from coming into contact with the plate 401 for pressing down the floating at the time of automatic re-inspection even if slight floating occurs, the measurement of the apparatus can be prevented from being stopped. When the sample container is surely pushed down, a level of an inclination terminal end of the slope may be set to a position lower than the lower surface of the plate 401. In other words, the push-down mechanism represented by the slope may push down the sample container to a level equal to or lower than the lower surface of the plate 401 for pressing down the floating. In addition, in FIG. 11, the slope 701 is integrated with the plate 401 for pressing down the floating, but the slope may be configured by a member other than the plate 401 for pressing down the floating. The integration can reduce the number of parts.

In addition, in the case of the automatic analyzing apparatus having multiple analyzers or in the case where the sample is suctioned at multiple suction positions even if only one analyzer is provided, if the sample container is floated from the rack between transports of the analyzers or between the suction positions, the floated sample container may come into the fixed plate to stop the apparatus or the probe may be damaged by a next analyzer or at a next suction position in the same manner as that described above. Therefore, it is desirable to push down the floated sample container to the rack regardless of whether there is a request for automatic re-inspection or not. In that case, it is desirable that at least the push-down mechanism 402 is located on the loading line 204 (sub-transport line). Furthermore, it is desirable to install the push-down mechanism 402 on the loading line 204 downstream of the sample suction position in a short time after the container has been floated up. After the sample container has been pushed down by the loading line 204, the sample container is transported from the loading line 204 to the loading/unloading line 205 (main transport line) with the result that the sample container is transported in a state where the floating of the sample container is improved.

In addition, since there is a possibility that the sample container is floated due to a vibration during transport of the sample rack or the like regardless of the number of suction positions and regardless of whether to perform re-inspection or not, a configuration in which the plate 401 for pressing down the floating is installed upstream of the suction position 207 as illustrated in FIG. 11 is effective.

Figure 12:
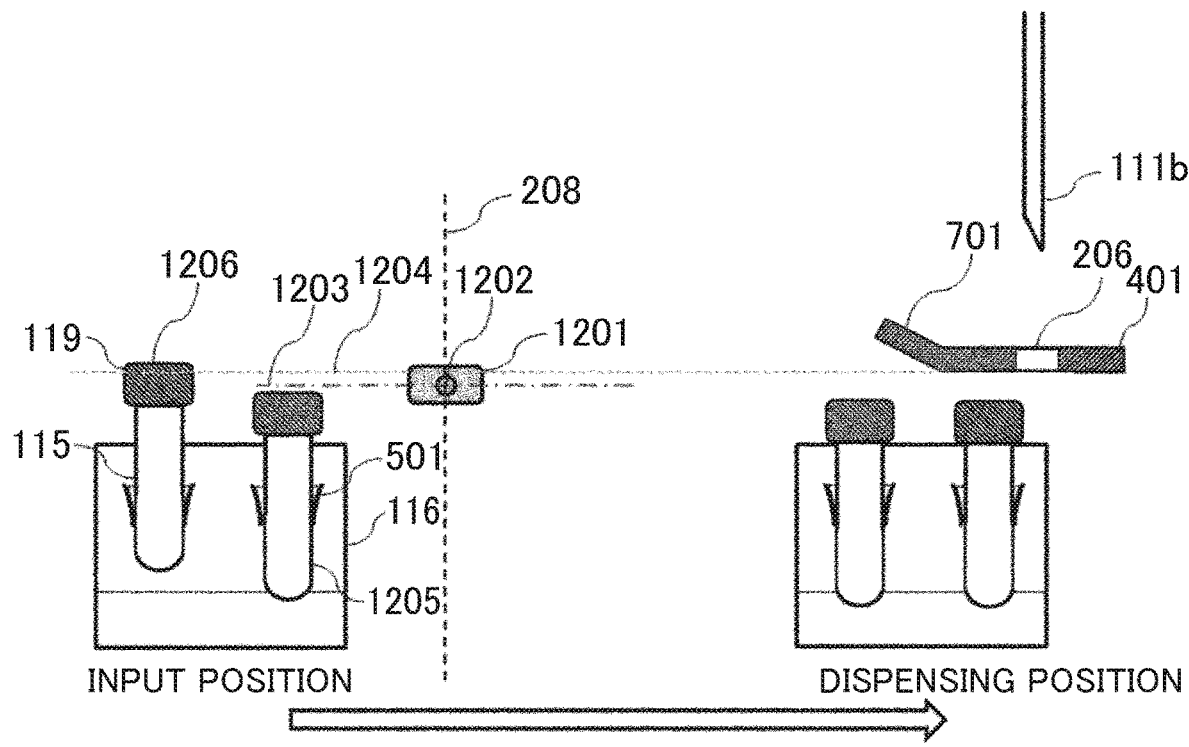
FIG. 12 is a diagram illustrating a relationship between a level measurement position of the sample container and a level of a plate that presses down floating.

In addition, as illustrated in FIG. 2, it is desirable that the level measurement position 208 of the sample container is placed between the loading port 201 and the rack loader 202. It is desirable that a sensor for measuring the level of the sample container is located at the measurement position, the level of the sample container is measured before the sample container moves to the suction position at the time of a first analysis, and the sample container, the level of which is equal to or more than a set value, is unloaded without being transported to the analyzer. The set value is arbitrarily settable, but there is a need to provide the set value lower than at least the level of the plate 401 for pressing down the floating. Then, the floated sample container is specified by the sensor, and the control unit 118 notifies a user of error information through a display unit or the like. With the above configuration, the sample container that has been floated for a reason other than the floating generated when pulling out the probe from the sample container can be prevented from being transported to the transport line 203 downstream of the rack loader 202. On the other hand, because the floating of the sample container cannot be monitored after the sample container has been loaded into the transport line 203 once, the mechanism 402 for pushing down the sample container to be described later is effective. FIG. 12 is a diagram illustrating a relationship between a level measurement position of the sample container and a level of a plate that presses down the floating. A sensor 1201 for measuring the level of the sample container is placed at the level measurement position 208 of the sample container. It is discriminated whether to notify the user of the error information with a sensor center 1202 as a boundary. A floating determination level set value 1203 and a plate level for pressing down the floating 1204 are levels shown. The set value 1203 is set to be lower than the level 1204. This is because the sample container is prevented from not getting under the plate 401, allowing the sample rack to stand still immediately before the suction position, and stopping the apparatus, for example, when the sample container higher than the level (level of the plate 401) of the sample container permitted by the apparatus is mounted on the sample rack. A difference between the levels 1203 and 1204 is a margin.

Also, the slope 701 starts from a position higher than the lower surface of the plate 401. With this configuration, even when the sample container whose level is not detected to be abnormal by the sensor 1201 is floated higher than the lower surface of the plate 401 after the sample container has passed through the position of the sensor 1201, the sample container can be effectively pushed down by the slope 701.

For example, if a sample container 1205 is equal to or less than a set value, the sample container 1205 is transported to the dispensing position without the detection of an abnormal level by the sensor 1201, and when the sample container is floated on the way, the sample container 1205 may be pushed down by the slope 701. However, in a sample container 1206 of a set value or more, the abnormal level is detected by the sensor 1201, the error information is notified the user of as described above, the sample container 1206 is not transported into the analyzing apparatus, and, for example, each rack is discharged from the transport line. This is because it is not distinguished whether the sample container higher than the allowable level of the apparatus is mounted on the rack, or the level of the sample container per se is allowable but detected by the sensor 1201 because the sample container is floated. In the latter, there is a possibility that the sample can be suctioned by the slope 701, but the determination in the apparatus is complicated taking such an event into consideration. Therefore, it is desirable to thus merely determine the level and notify the user of the error information. Incidentally, because the determination is performed not on a specimen unit but on a rack unit, in an example of FIG. 12, a right sample container is also discharged from the transport line due to a left sample container, and the example is not suctioned. The right and left sample racks indicate different sample racks.

As is apparent from FIGS. 2 and 12, a sensor 208 for detecting the level of the sample container is installed between the loading port 201 and the suction position 206 (207), and the slope is provided between the sensor 208 and the suction position 206 (upstream of the suction position 206). The sensor 208 is a sensor that detects the level lower than the lower surface of the plate 401, and the rack on which the sample container detected by the sensor 208 is mounted is discharged from the transport line without being transported to the suction position 206.

Meanwhile, the position of the sensor 208 is provided anywhere between the loading port 201 and the suction position 206, but it is desirable that the sensor 208 is located between the loading port 201 and the loading line 204. In addition, it is desirable that the rack on which the sample container detected by the sensor 208 is mounted is discharged without being transported to the loading line 204. This is because the rack is discharged without being transported to the loading line 204 eliminates the useless device operation of transporting the rack from the loading/unloading line 205 to the loading line 204, and so on. It is conceivable that the discharge of the rack is performed upstream of the rack loader disposed upstream of the loading/unloading line 205 or on the loading/unloading line 205.

As described above, with the combination of the sensor 1201 with the slope, since the unacceptable sample containers do not reach the plate 401, and only the sample containers that can be pushed down reach the plate 401, the apparatus can be reliably prevented from being stopped. Meanwhile, in this example, the slope is exemplified, but the same level relationship is applied to the other push-down mechanisms such as a rotor. In addition, the sensor 208 is configured by, for example, a known transmissive or reflective beam sensor, or the like.

In addition, FIG. 2 illustrates an example in which the sample rack 116 waits in the rack loader 202 until the inspection result is determined. However, the loader type may be replaced with a buffer type. Any type is applicable if the sample rack 116 can wait.

As has been described above, according to the present invention, there can be provided the automatic analyzing apparatus with high reliability in which the sample container that has been floated when pulling out the probe is pushed down to avoid contact of the floated sample container with the interior of the apparatus, and the probe is not damaged.

FIGS. 4 to 10 illustrate that the floated sample container is pushed down when actually pulling out the probe. FIG. 11 illustrates that the sample container floated when pulling out the probe, which has been further floated due to a vibration or the like, is pushed down to the plate 401, and that the sample container is pushed down to the plate 401 immediately before the plate 401 regardless of whether the probe is pulled out or not. In other words, "a mechanism that pushes down the sample container sealed with the floated sealing plug to the rack" defined in the claims is a mechanism that pushes down the sample container sealed with the sealing plug regardless of a cause of the float. This mechanism pushes down not only the containers that have been floated when pulling the probe, but also the containers further floated due to the vibration or the like from the position floated when pulling out the probe. A case in which the sample container is pushed down by a distance floated by a cause such as the vibration as a push-down amount is also involved in the "push-down mechanism" defined in the claims.

LIST OF REFERENCE SIGNS

101 . . . reaction disk, 102 . . . reaction vessel, 103 . . . cleaning mechanism, 104 . . . spectrophotometer, 105 . . . stirring mechanism, 106 cleaning bath (stirring mechanism), 107 . . . first reagent dispensing mechanism, 107a . . . second reagent dispensing mechanism, 108 . . . cleaning tank (reagent dispensing mechanism), 109 . . . reagent storage, 110 . . . reagent bottle, 111 . . . sample dispensing mechanism, 111a . . . sample dispensing mechanism, 111b . . . probe of sample dispensing mechanism, 112 . . . detergent bottle, 113 . . . cleaning tank (sample dispensing mechanism), 115 . . . sample container, 116 . . . sample rack, 117 . . . sample transport mechanism, 118 . . . control unit, 119 . . . rubber stopper, 201 . . . loading port, 202 . . . rack loader, 203 . . . transport line, 204 . . . loading line, 205 . . . loading/unloading line, 206 . . . suction position, 207 . . . suction position, 208 . . . level measurement position of sample container, 401 . . . plate for pressing down floating, 402 . . . push-down mechanism, 403 . . . spring, 404a . . . roller, 404b . . . roller, 501 . . . spring (sample rack), 601 . . . block, 602 . . . spring, 701 . . . slope, 801 . . . roller, 901a . . . roller, 901b . . . roller, 1001 . . . motor, 1002 . . . movable portion, 1003 . . . block, 1201 . . . sensor, 1202 . . . sensor center, 1203 . . . floating determination level set value, 1204 . . . plate level to press down floating, 1205 . . . sample container of set value or less, 1206 . . . sample container of set value or more

The invention claimed is:

1. An automatic analyzing apparatus including a transport line configured to transport a sample container mounted in a rack, and a probe that suctions a sample from the sample container at a suction position and discharges the sample into a reaction vessel, the probe pierces a sealing plug that seals the sample container, the automatic analyzing apparatus comprising: a member fixed at a predetermined level which presses down the sample container sealed with the sealing plug that is floated from the rack due to friction between the probe and the sealing plug upon the probe pulling out from the sample container sealed with the sealing plug; a mechanism that pushes down the sample container sealed with the sealing plug toward the rack upon transportation of the sample container on the transport line; and wherein the mechanism includes a contact portion that comes in contact with the floated sealing plug, and wherein the transport line transports the rack and the contact portion pushes down the floated sample container without stopping transportation of the rack.

2. The automatic analyzing apparatus according to claim 1,
wherein the mechanism includes an elastic member that is connected with the contact portion, and
the transport line transports the rack to compress the elastic member, and the contact portion pushes down the floated sample container by a compressed reaction.

3. The automatic analyzing apparatus according to claim 2,
wherein the contact portion includes a roller that rotates in a transport direction of the rack, and
an upper surface of the sealing plug of the floated sample container comes in contact with the roller, and the roller moves upward, and the roller pushes down the floated sample container by the reaction generated when compressing the elastic member.

4. The automatic analyzing apparatus according to claim 2,
wherein the contact portion includes a block having an inclination, a distance of which from the transport line is shorter toward a transport direction of the rack, an upper surface of the sealing plug of the floated sample container comes in contact with the block to move the block upward, and the block pushes down the floated sample container by the reaction generated when compressing the elastic member.

5. The automatic analyzing apparatus according to claim 1, wherein the contact portion has a shape in which the contact portion does not come into contact with a probe insertion/pull-out position of the sealing plug and comes in contact with a position of the sealing plug out of the insertion/pull-out position.

6. The automatic analyzing apparatus according to claim 1,
wherein the contact portion includes a slope having an inclination, a distance of which from the transport line is shorter toward a transport direction of the rack, an upper surface of the sealing plug of the floated sample container comes in contact with the slope to push down the floated sample container along the inclination of the slope.

7. The automatic analyzing apparatus according to claim 1, wherein the mechanism is disposed on an upstream side the suction position of the sample by the probe, and the mechanism pushes down the sample container to a level equal to or lower than that of a lower surface of the member.

8. The automatic analyzing apparatus according to claim 7, further comprising a level sensor for the sample container which is disposed between a loading port from which the rack is loaded and the suction position, wherein the mechanism is disposed between the level sensor and the suction position, the level sensor includes a sensor configured to detect a level lower than that of the lower surface of the member, and the rack on which the sample container detected by the level sensor is mounted is discharged from the transport line without being transported to the suction position.

9. The automatic analyzing apparatus according to claim 1,
wherein the contact portion includes a roller that rotates in a transport direction of the rack, an upper surface of the sealing plug of the floated sample container comes in contact with the roller, and the roller pushes down the floated sample container along a shape of the roller.

10. The automatic analyzing apparatus according to claim 1, wherein the mechanism includes a first contact portion and a second contact portion which come in contact with the sealing plug, and the second contact portion is disposed on a downstream side of the first contact portion in a transport direction of the rack, and a distance between the second contact portion and the transport line is shorter than a distance between the first contact portion and the transport line.

11. The automatic analyzing apparatus according to claim 1, further comprising:
a reagent storage that stores a reagent container;
a reaction disk having a reaction vessel that accommodates a mixed solution of the sample and the reagent;
a light source;
a spectrophotometer that receives light irradiated from the light source through the mixed solution; and
a control unit that outputs a concentration of a target component of the sample on the basis of an output of the spectrophotometer.

12. An automatic analyzing apparatus including a transport line configured to transport a sample container mounted on a rack, and a probe that suctions a sample from the sample container at a suction position and discharges the sample into a reaction vessel, the probe pierces a sealing plug that seals the sample container, the automatic analyzing apparatus comprising: a member fixed at a predetermined level which presses down the sample container sealed with the sealing plug that is floated from the rack due to friction between the probe and the sealing plug upon the probe pulling out from the sample container sealed with the sealing plug; a mechanism that pushes down the sample container sealed with the floated sealing plug toward the rack upon transportation of the sample container by the transport line after pulling out the probe from the sample container sealed with the sealing plug; wherein the mechanism includes a contact portion that comes in contact with the floated sealing plug, and wherein the transport line transports the rack and the contact portion pushes down the floated sample container without stopping transportation of the rack.

13. The automatic analyzing apparatus according to claim 12,
wherein the transport line includes a main transport line and a sub-transport line disposed adjacent to the main transport line,
the rack is transported to the sub-transport line through the main transport line,
the probe suctions the sample from the sample container at the sample suction position on the sub-transport line,
the mechanism is disposed on the sub-transport line downstream of the sample suction position, and
after the sample container sealed with the floated sealing plug is pushed down by the mechanism, the rack is transported from the sub-transport line to the main transport line.

14. The automatic analyzing apparatus according to claim 12,
wherein the transport line includes a main transport line and a sub-transport line disposed adjacent to the main transport line,
the rack is transported to the sub-transport line through the main transport line,
the probe suctions the sample from the sample container at the sample suction position on the sub-transport line,
the mechanism is disposed on the sub-transport line upstream of the sample suction position, and
after the sample container sealed with the floated sealing plug is pushed down to a level equal to or lower than a lower surface of the member by the push-down mechanism, the sample is suctioned at the sample suction position.

* * * * *